US006274777B1

(12) United States Patent
Gray et al.

(10) Patent No.: US 6,274,777 B1
(45) Date of Patent: Aug. 14, 2001

(54) METHOD FOR REMOVING BORON FROM POLYALKYL HYDROXYAROMATICS

(75) Inventors: James A. Gray, Novato, CA (US); Thierry Triconnet, Saint Romain de Colbosc (FR)

(73) Assignees: Chevron Chemical Company LLC, San Francisco, CA (US); Chevron Chemical S.A., Levallois-Perret (FR)

( * ) Notice: Subject to any disclaimer, the term of this patent is extended or adjusted under 35 U.S.C. 154(b) by 0 days.

(21) Appl. No.: 09/475,913

(22) Filed: Dec. 30, 1999

(51) Int. Cl.[7] .................................................. C07C 37/68
(52) U.S. Cl. ............................................ 568/792; 568/790
(58) Field of Search .................................... 568/792, 790; 528/205, 86

(56) References Cited

U.S. PATENT DOCUMENTS

| | | | |
|---|---|---|---|
| 3,000,964 | 9/1961 | Milligan | 260/624 |
| 3,371,075 | * 2/1968 | Mears, Jr. et al. | . |
| 3,917,733 | 11/1975 | Winter, III | 260/674 SA |
| 4,045,507 | 8/1977 | Cupples et al. | 260/683.15 B |
| 4,152,499 | 5/1979 | Boerzel et al. | 526/52.4 |
| 4,263,467 | 4/1981 | Madgavkar et al. | 585/525 |
| 4,384,162 | 5/1983 | Vogel et al. | 585/830 |
| 4,433,197 | 2/1984 | Vogel et al. | 585/823 |
| 4,507,475 | 3/1985 | Straehle et al. | 536/120 |
| 4,528,364 | 7/1985 | Prier | 528/370 |
| 4,587,307 | 5/1986 | Bronstert et al. | 525/362 |
| 4,956,513 | 9/1990 | Walker et al. | 585/525 |
| 4,981,578 | 1/1991 | Tycer et al. | 208/262.1 |
| 5,003,111 | 3/1991 | Harper | 568/618 |
| 5,055,496 | 10/1991 | Harper | 521/174 |
| 5,300,701 | 4/1994 | Cherpeck | 568/792 |
| 5,876,468 | 3/1999 | Moreton | 44/415 |

FOREIGN PATENT DOCUMENTS

| | | | |
|---|---|---|---|
| 1159368 | 7/1969 | (GB) | C08F/27/00 |
| 3-195728 | 8/1991 | (JP) | C08G/65/30 |
| 4-197407 | 7/1992 | (JP) | B01D/36/00 |
| 9-176073 | 7/1997 | (JP) | C07C/43/15 |

OTHER PUBLICATIONS

CA:76:142782 abs of IN 123209, Aug. 1971.*

* cited by examiner

Primary Examiner—Jean F. Vollano
(74) Attorney, Agent, or Firm—Claude J. Caroli

(57) ABSTRACT

A method for removing boron from a boron trifluoride-catalyzed polyalkyl hydroxyaromatic reaction product which comprises:

(a) diluting the polyalkyl hydroxyaromatic reaction product with an inert solvent to give a polyalkyl hydroxyaromatic reaction product concentration in the range of about 40 to about 80 weight percent;

(b) filtering the diluted polyalkyl hydroxyaromatic reaction product in the presence of a filter aid in combination with (1) magnesium silicate, (2) water or (3) a mixture of magnesium silicate and water; wherein the water is present during filtration at a concentration of about 100 to 1,500 ppm, based on the diluted polyalkyl hydroxyaromatic reaction product; with the proviso that when water is used in the absence of magnesium silicate, the filter aid is diatomaceous earth; and (c) recovering a filtrate containing the diluted polyalkyl hydroxyaromatic reaction product having less than about 10 ppm of boron present.

18 Claims, No Drawings

METHOD FOR REMOVING BORON FROM POLYALKYL HYDROXYAROMATICS

BACKGROUND OF THE INVENTION

1. Field of the Invention

This invention relates to a method for removing boron from polyalkyl hydroxyaromatic compounds. More particularly, this invention relates to removing boron from boron trifluoride-catalyzed polyalkyl hydroxyaromatic reaction products to levels below about 10 parts per million (ppm) by filtering the polyalkyl hydroxyaromatic reaction product with a solid filtering agent having an active surface.

2. Description of the Related Art

Boron trifluoride is used as a catalyst in relatively low concentrations for synthesis of liquid hydrocarbons from various olefins. Example applications are alkylation of hydroxyaromatic compounds with various olefins, oligomerization of alpha olefins, and polymerization of low molecular weight olefins. Many of these products find application in lubricating oil additives and gasoline or diesel fuel additives. The boron trifluoride may be introduced into the reaction as a gas or as a complex (for example, boron trifluoride-etherate, boron trifluoride-phenol, and many others). Depending on the particular process, the boron trifluoride is present in the reaction mixture as dissolved gas, or a coordination compound or a mixture of the two forms.

A common feature of all of these processes is that the boron trifluoride must be removed after the reaction, either in a form that can be recycled or in a form that requires disposal. Depending upon the molecular weight and the viscosity of the product, further processing such as distillation can be limited by the presence of boron trifluoride in the product because it will cause depolymerization and cracking of olefin polymers at elevated temperatures. There have been three general techniques used that may or may not involve chemical reaction of the boron trifluoride; adsorption on a particulate solid and separation from the reaction product, extraction using various aqueous solutions and phase separation from the reaction product, and removal by distillation or stripping. Combination of these processes can also be used.

U.S. Pat. No. 4,045,507 describes a process in which 1-decene is oligomerized to a product containing primarily trimer and tetramer in a reactor pressurized with boron trifluoride and containing a coordination compound formed by complexing boron trifluoride with a suitable polar compound such as n-butanol. The resulting oligomer product solution contains boron trifluoride that must be separated from the product. U.S. Pat. No. 4,433,197 discusses a method of selective removal of the boron trifluoride from oligomer product leaving behind the polar compound (n-butanol) used to form the coordination compound. The boron concentration was reduced to a concentration of 13–32 ppm from an initial concentration of 0.5% using silica as a solid absorbent. Recovery of the boron trifluoride was then accomplished by extraction from the silica using n-butanol. A bed of granular polyvinyl alcohol was shown in U.S. Pat. No. 4,384,162 to be another effective adsorbent for nondestructive removal and recycle of boron trifluoride.

U.S. Pat. No. 3,917,733 gives a process scheme for removing boron oxide hydrate from a liquid aromatic hydrocarbon stream and the boron trifluoride off-gas from the alkylation zone using a moving bed of particulate alumina. No mention is made of recovering the boron trifluoride.

Solid reactants that neutralize and extract the boron trifluoride from reaction product have also been widely illustrated in the patent literature. In a 1-olefin oligomerization process, U.S. Pat. No. 4,981,578 discloses that potassium fluoride (KF) in either particulate solid or aqueous solution form can be reacted with the boron trifluoride ($BF_3$) in the oligomer product solution. This reaction yields a solid precipitate of potassium fluoborate ($KBF_4$) that can then be filtered from the oligomer product. The aqueous solution approach reduced the boron from an initial level of 820 ppm in the oligomer product to 63 ppm after treatment. Similarly, a bed of KF reduced the boron concentration from 820 ppm before treatment to 6 ppm after treatment. This patent teaches that sodium fluoride (NaF) or ammonium fluoride ($NH_4F$) may also be used instead of KF.

In a cracked-petroleum-fraction olefin polymerization process, U.S. Pat. No. 3,371,075 illustrates the use of particulate hydrated lime and fuller's earth (more than 90% natural attapulgite and montmorillonite) for neutralization and removal of boron trifluoride catalyst as well as decolorization of the product. The crude product containing the boron trifluoride is mixed with the hydrated lime and fuller's earth and then filtered. Boron was reduced from an initial concentration of approximately 540 ppm to about 4 ppm in the finished product.

In another 1-olefin oligomerization process using boron trifluoride, U.S. Pat. No. 4,956,513 discloses a simple water extraction method for directly removing boron trifluoride. In this method the crude product is washed with water and the phases separated. This is done twice and the aqueous phase washings are combined, then distilled to concentrate the $BF_3$—$H_2O$ complex and recover water and n-butanol overhead. $BF_3$ can then be recovered by mixing concentrated oleum or sulfur trioxide with the distillation bottoms.

Examples of water extraction applied to boron trifluoride removal from crude polyisobutylphenol, made from alkylation of phenol with polybutene, can be found in U.S. Pat. Nos. 5,300,701, 5,876,468, and British Patent GB 1,159,368. In the examples in these patents, the crude product is mixed with aqueous ammonia to neutralize the $BF_3$ and then the product is extracted several times with water. The British Patent GB 1,159,368 further teaches that the $BF_3$ can be neutralized with ammonia gas and then the $BF_3$—$NH_3$ salt filtered from the crude polyisobutyl phenol.

Distillation techniques have also been used for boron trifluoride recovery of the 1-olefin oligomerization reaction mixture. In U.S. Pat. No. 4,263,467, the crude oligomer mixture exits the reaction zone and is then fed downward through a column packed with Berl saddles, a trickle-bed column, while maintaining a pressure of 203 mm of mercury on the column at 23° C. The boron trifluoride is recovered overhead as a gas. The concentration of $BF_3$ in the product is reduced from an initial level of 2.77% to a concentration after stripping of 680 ppm.

Another distillation approach to recover $BF_3$ catalyst is disclosed in U.S. Pat. No. 3,000,964 for a phenol alkylation process. In this method, an entrainer constituent such as heptane is refluxed in the crude alkyphenol distillation column. The entrainer distills overhead and carries the $BF_3$ overhead with it. The entrainer is returned to the column while the $BF_3$ is absorbed into liquid phenol that is used to transport the $BF_3$ back to the alkylation reactor. The alkylphenol is the distillation column bottoms product. There is no mention in this patent of residual boron concentration in the product or subsequent treating to remove trace contaminants.

The removal of alkaline catalysts from various polyether polyols is also known in the art. For example, U.S. Pat. No.

4,528,364 to Prier discloses a method of removing alkaline catalysts from polyether polyols and polyalkylene carbonate polyols which comprises dissolving the polyol in an aprotic solvent and then contacting the polyol solution with a sufficient amount of an adsorbent to adsorb the alkaline catalysts, followed by physically separating the adsorbent from the polyol solution. This patent teaches that the process described therein is advantageous as there is no water present to hydrolyze either the polyether polyol or the polyalkylene carbonate polyol. This patent further teaches that preferred adsorbents are aluminum and alkaline earth metal silicates, with magnesium silicate being most preferred. Suitable catalysts taught by this patent include alkali metal borates, alkaline earth metal borates and ammonium borates.

U.S. Pat. No. 4,507,475 to Straehle et al. discloses a process for purifying crude polyether polyols prepared by anionic polymerization of alkylene oxides in the presence of basic catalysts, wherein the polyols are mixed with water and ortho-phosphoric acid in certain quantity ratios, an adsorption agent is incorporated in the reaction mixture, the mixture is filtered and the water is removed from the polyol by distillation. This patent teaches that the polyol is mixed with 0.2 to 1.5 parts by weight of water per 100 parts of polyol and that the water content is of decisive important for the quantity of the purification. This patent further teaches that commonly used catalysts are alkali alkoxides and alkali hydroxides, preferably potassium hydroxide. Preferred adsorption agents taught by this patent are natural and synthetic silicas of earth alkali metals or aluminum, preferably synthetic magnesium silicate. This patent also teaches that it is advantageous to use filtration aids such as perlite, kieselguhr and diatomaceous earths, in addition to the adsorption agents.

U.S. Pat. Nos. 5,003,111 and 5,055,496, both to Harper, disclose a process for preparing polyether polyols by polymerizing isobutylene oxide with other alkylene oxides in the presence of an alkali metal catalyst and a crown ether cocatalyst to afford polyols containing low levels of unsaturation. These patents teach that the alkali metal may be derived from any suitable source, including alkali metal hydroxides, alkoxides and phenoxides, and that the alkali metal is preferably potassium or sodium. These patents further teach that the crude polyether polyol is treated to separate the alkali metal and crown ether from the product and that contacting the crude polyol with an adsorption agent, such as magnesium silicate, effectively reduces the alkali metal and crown ether content to acceptable levels. In the examples, these patents teach that the crude polyol was treated with 4% magnesium silicate, 0.5% water and 1% diatomaceous earth for four hours at 110° C. to remove potassium hydroxide and crown ether. The polyol was then filtered through diatomaceous earth, diluted with toluene, water washed and vacuum stripped to provide the final polyol.

Japanese Kokai (laid-open) Patent Application No. HEI 3-195728 (1991) discloses a process for the purification of polyoxyalkylene polyol which has been synthsized in the presence of alkaline catalyst, which involves neutralizing the crude polyol with mineral acid to a pH of 4.5 to 7.5, followed by adsorption with a synthetic magnesium silicate containing less than 0.5 weight percent sodium, wherein the amount of synthetic magnesium silicate used as adsorbent is 0.05 to 5 weight percent of the polyol. The catalysts used in the polyol synthesis are described as potassium hydroxide, sodium hydroxide, potassium alcoholate, sodium alcoholate, potassium carbonate, sodium carbonate, metallic potassium and metallic sodium.

Japanese Kokai (laid-open) Patent Application No. HEI 4-197407 (1992) discloses a process for the purification of polyethers, in which catalyst is removed from crude polyethers having a high viscosity, which involves an adsorption treatment performed by the addition of a magnesium silicate adsorbent having an average particle diameter of above 100 micrometers to the crude polyether product, followed by filtration through a filter precoated with a filter aid consisting of diatomaceous earth having an average particle diameter of more than 100 micometers. Catalysts disclosed for use in the synthesis of the crude polyethers include alkaline catalysts, such as potassium hydroxide and sodium hydroxide, and complex metal cyano compounds, such as zinc hexacyano cobaltate complex and zinc hexacyano iron complex. The complex metal cyano compounds are preferred for making polyether polyols of 8,000 to 50,000 molecular weight.

Japanese Kokai (laid-open) Patent Application No. HEI 9-176073 (1997) discloses a process for manufacturing a propenyl ether compound in which an allyl ether compound is subjected to a rearrangement reaction with the use of an alkali metal hydroxide and/or alkaline earth metal hydroxide as a catalyst, wherein a silicate type adsorbent is used for catalyst removal and purification. This publication teaches that the adsorbent may be selected from acid clay, zeolite, synthetic magnesium silicate, synthetic aluminosilicate, and synthetic magnesium aluminosilicate. This publication further teaches that improved efficiency of catalyst removal can be obtained by the addition of water during the catalyst removal and purification period, wherein the weight ratio of water to silicate adsorbent is from 20:100 to 500:100.

It is known in the art that trace concentrations of contaminants remaining in an intermediate after synthesis can have a very detrimental effect on downstream processing. A good example of this problem is illustrated in U.S. Pat. No. 4,587,307. It is well known that polyisobutene is an intermediate in the manufacture of additives for lubricating oil and fuel applications. In one such use, polyisobutene can be combined with maleic anhydride to give a long-chain succinic anhydride. This can then be further derivatized with amines or polyamines to give the corresponding amides or imides. However, polyisobutenes obtained, for example, by the process described in U.S. Pat. No. 4,152,499 contain small quantities of substances not known in detail. These substances are present in the polyisobutene after the removal of the $BF_3$ catalyst and readily volatile constituents. When the polyisobutene is used in a reaction with maleic anhydride, these unknown substances also react with the maleic anhydride forming deposits on the walls and internal parts of the reaction vessels. This results in reduced product quality and problems in maintaining the operability of the equipment. U.S. Pat. No. 4,587,307 addresses this problem by utilizing a method for treating the polyisobutene over a bed of solid adsorbent at 50–280° C. The adsorbents include aluminum oxide, partially or fully hydrated aluminum oxide, boron oxide, partially or fully hydrated boron oxide, titanium oxide, partially or fully hydrated titanium oxide, or any combination of this group. Completely or partially hydrated silicon dioxide may be used at 20–280° C.

An example in U.S. Pat. No. 4,587,307 describes a polyisobutene of number average molecular weight 1000 that was prepared by polymerization of isobutene at 20° C. using 0.2 mole % $BF_3$ as a catalyst. The polymer was freed from the catalyst in what is described as a "conventional manner" but no details were given in the patent example. However, the background section of this patent defines "conventional manner" as encompassing termination of the polymerization by adding water or an alcohol; filtering off solid residues or adsorbing them onto an adsorbent such as aluminum oxide; or, as an alternative, extracting catalysts with water, a base or methanol. In the patent example, low molecular weight constituents were removed by distillation at 200° C. and subatmospheric pressure. The polyisobutene was then passed through a bed of acidic $Al_2O_3$ having a mean particle size of 0.15 mm. The mean contact time was 20 minutes. No deposits were formed on the reaction vessel walls when a sample of this polyisobutene was reacted with maleic anhydride at 225° C. in a stainless steel autoclave for 4 hours. By comparison, in a controlled experiment, polyisobutene that had not been treated with the acidic $Al_2O_3$ led to the formation of deposits in the reaction with maleic anhydride.

SUMMARY OF THE INVENTION

The present invention provides a method for removing boron from a boron-trifluoride catalyzed polyalkyl hydroxyaromatic reaction product which comprises:

(a) diluting the polyalkyl hydroxyaromatic reaction product with an inert solvent to give a polyalkyl hydroxyaromatic reaction product concentration in the range of about 40 to about 80 weight percent;

(b) filtering the diluted polyalkyl hydroxyaromatic reaction product in the presence of a filter aid in combination with (1) magnesium silicate, (2) water or (3) a mixture of magnesium silicate and water; wherein the water is present during filtration at a concentration of about 100 to 1,500 ppm, based on the diluted polyalkyl hydroxyaromatic reaction product; with the proviso that when water is used in the absence of magnesium silicate, the filter aid is diatomaceous earth; and (c) recovering a filtrate containing the diluted polyalkyl hydroxyaromatic reaction product having less than about 10 ppm of boron present.

In the present invention, the polyalkyl hydroxyaromatic reaction product is preferably diluted with the inert solvent to give a polyalkyl hydroxyaromatic reaction product concentration in the range of about 50 to about 80 weight percent, more preferably about 60 to about 75 weight percent, and most preferably about 65 to about 70 weight percent. The preferred filter aid employed in the present method is diatomaceous earth. When utilized, water is present during filtration at a preferred concentration of about 200 to 1200 ppm, and more preferably about 250 to 1000 ppm, based on the diluted polyalkyl hydroxyaromatic reaction product. Preferred polyalkyl hydroxyaromatic reaction products include polypropyl phenol and polyisobutyl phenol, especially polyisobutyl phenol.

Among other factors, the present invention is based on the discovery that boron can be effectively removed from boron-trifluoride catalyzed polyalkyl hydroxyaromatic reaction products to levels below about 10 ppm by filtering the crude polyalkyl hydroxyaromatic reaction product with a solid filtering agent having an active surface. This is particularly surprising since conventional filtration technology can typically only lower the boron content to levels of about 45 to 80 ppm. However, boron levels as low as 30 ppm have been found to cause unwanted side reactions and product degradation when the boron-containing polyalkyl hydroxaromatic compounds are used as intermediates to manufacture other products, such as Mannich bases. The present invention eliminates the problems associated with high boron levels in subsequent processing steps, while avoiding the need for extensive water washing and wastewater removal.

Accordingly, in a further aspect of the present invention, the diluted polyalkyl hydroxyaromatic reaction product having less than about 10 ppm of boron present is further reacted with an aldehyde and a polyamine to provide a Mannich condensation product having no resin deposits in the reactor.

A typical hydroxyaromatic alkylation reaction example is the synthesis of polyisobutyl phenol. In this synthesis there are four major process steps; (1) reaction of phenol in excess of stoichiometric with polyisobutene in the presence of boron trifluoride catalyst, (2) neutralization of the catalyst after the reaction period is completed, (3) removal of the excess phenol by distillation, and (4) removal of the neutralized catalyst by water washing or filtration. Water washing is well known in this field as a means of removing the boron to levels below 5 ppm. However, this generates a lot of wastewater and presents an expensive waste disposal problem in many manufacturing locations. We made the surprising discovery that filtration using various grades of diatomaceous earth filter aid typically can only remove the boron to levels of about 45–80 ppm by using excess filter aid and depending on how low a filtration rate and how much solid waste can be tolerated. We also discovered that polyisobutylphenol containing boron in the 30–100 ppm range creates a major problem with resin deposition on equipment and color formation when it is reacted with formaldehyde and polyethylene amines to make a Mannich base. Therefore, a process for removing boron from high molecular weight alkylphenol to levels below 10 ppm would eliminate the problems associated with boron in subsequent processes and at the same time reduce the amount of aqueous and solid waste in trying to remove boron.

DETAILED DESCRIPTION OF THE INVENTION

The present invention is concerned with the removal of boron, primarily in the form of boron trifluoride salts, from crude polyalkyl hydroxyaromatic compounds. These compounds are prepared by alkylating a hydroxyaromatic compound with a polyolefin in the presence of a boron-trifluoride acidic alkylation catalyst, including free boron trifluoride and boron trifluoride complexes. The method of the present invention also imparts improved properties to the polyalkyl hydroxyaromatic compound in subsequent processing steps, such as the reaction with an aldehyde and a polyamine to provide a Mannich condensation product.

In general, the polyalkyl substituent on the polyalkyl hydroxyaromatic compound will have a number average molecular weight in the range of about 300 to 5,000, preferably about 400 to 3,000, more preferably from about 500 to 2,000.

The polyalkyl-substituted hydroxyaromatic compounds employed in this invention are derived from hydroxyaromatic hydrocarbons. Such hydroxyaromatic compounds include mononuclear monohydroxy and polyhydroxy aromatic hydrocarbons having 1 to 4, and preferably 1 to 3, hydroxy groups. Suitable hydroxyaromatic compounds include phenol, cathechol, resorcinol, hydroquinone, pyrogallol, and the like. The preferred hydroxyaromatic compound is phenol.

Suitable polyalkyl hydroxyaromatic compounds and their preparation are described, for example, in U.S. Pat. Nos. 4,231,759 and 4,238,628, the disclosures of each of which are incorporated herein by reference.

The polyalkyl substituent on the polyalkyl hydroxyaromatic compounds employed in the invention may be generally derived from polyolefins which are polymers or copolymers of mono-olefins, particularly 1-mono-olefins, such as ethylene, propylene, butylene, and the like. Preferably, the mono-olefin employed will have 2 to about 24 carbon atoms, and more preferably, about 3 to 12 carbon atoms. More preferred mono-olefins include propylene, butylene, particularly isobutylene, 1-octene and 1-decene. Polyolefins prepared from such mono-olefins include polypropylene, polybutene, especially polyisobutene, and the polyalphaolefins produced from 1-octene and 1-decene.

The preferred polyisobutenes used to prepare the presently employed polyalkyl hydroxyaromatic compounds are polyisobutenes which comprise at least about 20% of the more reactive methylvinylidene isomer, preferably at least 50% and more preferably at least 70% methylvinylidene isomer. Suitable polyisobutenes include those prepared using $BF_3$ catalysts. The preparation of such polyisobutenes in which the methylvinylidene isomer comprises a high percentage of the total composition is described in U.S. Pat. Nos. 4,152,499 and 4,605,808.

Examples of suitable polyisobutenes having a high alkylvinylidene content include Ultravis 10, a polyisobutene having a molecular weight of about 950 and a methylvinylidine content of about 76%, and Ultravis 30, a polyisobutene having a molecular weight of about 1300 and a methylvinylidene content of about 74%, both available from British Petroleum, and Glissopal 1000, 1300 and 2200, available from BASF.

Numerous methods are known for preparing the polyalkyl hydroxyaromatic compounds used in the present invention. For example, U.S. Pat. No. 4,231,759 discloses that polyalkyl hydroxyaromatic compounds may be obtained by the alkylation of phenol with polypropylene, polybutylene and other polyalkylene compounds, in the presence of an alkylation catalyst, such as boron trifluoride.

Another method of preparing polyalkyl hydroxyaromatic compounds is disclosed in U.S. Pat. No. 4,238,628. This patent teaches a process for producing undegraded alkylated phenols by alkylating at about 0° C. to 60° C., a complex comprising boron trifluoride and phenol with a propylene or higher olefin polymer having terminal ethylene units, wherein the molar ratio of complex to olefin polymer is about 1:1 to 3:1. Preferred olefin polymers include polybutene having terminal ethylene units.

Preferred polyalkyl hydroxyaromatic compounds finding use in the method of the present invention include polypropylene phenol, polyisobutylene phenol, and polyalkyl phenols derived from polyalphaolefins, particularly 19-decene oligomers.

Polyalkyl phenols, wherein the polyalkyl group is derived from polyalphaolefins, such as 1-octene and 1-decene oligomers are described in PCT International Patent Application Publication No. WO 90/07564, published Jul. 12, 1990, the disclosure of which is incorporated herein by reference. This publication teaches that such polyalkyl phenols may be prepared by reacting the appropriate polyalphaolefin with phenol in the presence of an alkylating catalyst at a temperature of from about 60° C. to 200° C., either neat or in an inert solvent at atmospheric pressure.

The boron-trifluoride acidic alkylation catalyst used to alkylate the hydroxyaromatic compound is typically in the form of free boron trifluoride or a boron trifluoride complex. Suitable boron trifluoride complexes include boron trifluoride etherate, boron trifluoride-phenol and boron trifluoride-phosphoric acid.

In general, the reaction temperature for the alkylation reaction will be in the range of about 0° C. to 200° C., preferably in the range of about 0° C. to 100° C., and more preferably in the range of about 20° C. to 60° C. The reaction pressure will generally be atmospheric, although higher or lower pressures may be employed.

The molar ratio of the hydroxyaromatic compound to polyolefin is normally in the range of about 1.2:1 to 5:1, and preferably will be in the range of about 2:1 to 3:1. In general, the number of equivalents of the acidic alkylation catalyst per equivalent of polyolefin will be in the range of about 0.005:1 to 5:1, and preferably in the range of about 0.025:1 to 0.6:1.

The alkylation reaction may be carried out neat or in the presence of a solvent which is inert to the reaction of the hydroxyaromatic compound and the polyolefin. When employed, a typical solvent is hexane.

The alkylation reaction will generally be carried out over a period of about 2 to 48 hours, and preferably over a period of about 3 to 20 hours.

U.S. Pat. No. 5,300,701 to Cherpeck describes a $BF_3$-catalyzed process for alkylating phenol with polyisobutene which utilizes a purification procedure for the crude polyisobuyl phenol reaction product involving neutralization of the $BF_3$ or $BF_3$-complex catalyst with aqueous ammonia and repeated washing with water. However, this is not a practical method in a commercial operation. When the preferred charge mole range of 2:1 to 5:1 of phenol:polyisobutene is used to conduct the reaction, there is considerable phenol left over that must be recovered and reused to make the process economically viable. The excess phenol cannot be simply distilled from the crude product at elevated temperature in the presence of $BF_3$ or $BF_3$-complex. At temperatures of about 65° C. and higher, a considerable amount of depolymerization and cracking will occur, degrading the desired product. The desired reaction conditions have been described in British Patent GB 1,159,368. The end result is the generation of byproducts of t-butylphenol, di-t-butylphenol and other light alkylphenol analogs along with further unnecessary consumption of phenol. This problem can be resolved by neutralizing the $BF_3$ or $BF_3$-complex with a base such as ammonia gas or aqueous ammonia prior to the distillation. The use of an ammonia gas neutralization method in hydroxyaromatic alkylation with olefins has been disclosed in French Patent No. 827,469 to Standard Oil Development Company. After neutralization, it is safe to increase the polyisobutyl phenol temperature above 60° C. without undergoing depolymerization. The crude polyisobutyl phenol is distilled by raising the temperature to about 160–170° C. and lowering the pressure to about 20–40 mm of mercury so as to distilled the unconverted phenols and light alkylphenols overhead and leave behind the desired polyisobutylphenol and boron salts.

It is known in the art that water washing will generally be adequate to remove the boron salts to very low levels (less than about 5 ppm boron). However, in many manufacturing locations throughout the world, it is more desirable to filter sediment from a product rather than generate considerable fluorine-containing wastewater that must be treated and disposed. Accordingly, it would be advantageous to filter the sediment from the crude distilled polyisobutylphenol after distillation and have less than about 10 ppm of boron remaining in the finished product.

However, it has now been found that conventional filtration is only sufficient to reduce the boron concentration to about 45–80 ppm when purifying crude polyisobutyl phenol. Increasing the amount of filter aid and reducing the particle size of the filter aid was not successful in lowering the boron concentration further. It is now believed that part of the boron salt residue may be present in a soluble or complexed form that can pass through the filter. The present invention addresses this problem and allows substantially all of the boron salt to be filtered from the distilled, crude polyisobutyl phenol.

As an example of the present process, the procedure for treating distilled crude polyisobutyl phenol is described as follows. Distilled, crude polyisobutyl phenol, typically containing about 0.2% boron salts, is charged to a tank with an agitation system, typically a filter-feed tank. A solvent such as Exxon Aromatic 100 or Total Solvarex 9 (a $C_9$ aromatic solvent) is added to the tank and mixed with the polyisobutyl phenol so as to lower its viscosity and facilitate thorough mixing when the solids are charged. Other solvents which may be employed include typical aromatic solvents, such as toluene or xylene, and aliphatic solvents such as decane, dodecane, hexadecane, cyclohexane, methylcyclopentane, and the like. The dilution with solvent is sufficient to give a polyisobutyl phenol concentration in the range of about 40–80% by weight, preferably about 50–80% by weight, more preferably about 60–75% by weight, and most preferably about 65–70% by weight. The temperature is adjusted in the range of about 20–200° C., depending on the solvent boiling range and to some extent upon the solvent flash point for particular equipment. The preferred temperature range is about 35–100° C., and more preferably about 40–55° C. This temperature is used throughout the rest of the treatment. The temperature adjustment and solvent addition may be done at the same time. It typically requires 0.25–1.5 hours to mix the solvent and distilled crude polyisobutyl phenol. The mixture of solvent and crude polyisobutyl phenyl is then filtered in accordance with the present invention. A comparison of conventional filtration with the method of the present invention follows below.

Conventional Filtration

After adjusting the diluted crude polyisobutyl phenol temperature and concentration in solvent, 0.2–0.6% diatomaceous earth filter aid, based on the diluted crude polyisobutyl phenol, is added to the diluted crude and mixed for about 1–2 hours until the mixture is uniform. Typical diatomaceous earth filter aids include HyFlo Super Cel and Celite 512 sold by Mansville Corporation in the United States, and Clarcel CBL-CB or Clarcel CBL-DIC sold by CECA in Europe. Prior to starting filtration, a precoat layer of 2–3 mm thickness is put on a pressure filter screen or media by circulating a dilute suspension of one of the previous filter aids in solvent through the filter many times. In a small-scale laboratory test, the precoat may be put on the filter media dry. In either case, filtrate may be recycled until it is clear in appearance when the filtration is started. The crude product is fed to the filter and filtered under pressure up to 100 psig. Typical final filtration pressures are in the range of 40–90 psig. The filtrate containing the diluted polyisobutyl phenol is collected and analyzed for boron.

Magnesium Silicate Method

After adjusting the diluted crude polyisobutyl phenol temperature and concentration in solvent, 0.05–2% of magnesium silicate, such as Magnesol, a synthetic magnesium silicate manufactured by The Dallas Group of America is mixed with the diluted crude. One of the diatomaceous earth filter aids described above is also charged. The amount of filter aid charged is in the range of 0.005–1%, based on the diluted crude polyisobutyl phenol. The purpose of the filter aid is to improve the filtration rate of the magnesium silicate. The amount of filter aid required will depend on the filtration characteristics of the grade of magnesium silicate used. The preferred charge of magnesium silicate is 0.1–0.7%, and the most preferred charge is 0.2–0.4%, based on the diluted crude polyisobutyl phenol. The preferred range of filter aid is 0.02–0.4%, and the most preferred range is 0.04–0.2%.

Typically, about 10 to 100 grams of magnesium silicate will be employed per gram of boron to be removed, preferably about 25 to 85 grams, and more preferably about 25 to 50 grams of magnesium silicate per gram of boron. In general, about 2 to 20 grams of filter aid will also be employed per gram of boron to be removed, preferably about 4 to 15 grams, and more preferably about 4 to 8 grams of filter aid per gram of boron.

Suitable filter aids for use in the present invention include diatomaceous earth (diatomite, kieselguhr, infusorial earth), perlite, asbestos fibers, such as chrysotile, cellulose fibers, such as Solka Floc, carbon-based filter aids, fly ash, and plastics, such as Gellfilt, made from foamed polyurethane. Mixtures of filter aids may also be employed. A preferred filter aid is diatomaceous earth.

The charge order of the magnesium silicate and the filter aid is not particularly significant. However, the degree of mixing is an important consideration. The magnesium silicate and filter aid should be mixed to uniformity in the diluted polyisobutyl phenol with no settling in the bottom of the tank.

The magnesium silicate, filter aid, and diluted crude polyisobutyl phenol are mixed for 0.25–10 hours, preferably for 0.5–3 hours, and most preferably 1–2 hours, at the temperature ranges described above, that is, about 20–200° C., preferably about 35–100° C., and more preferably about 40–55° C.

A precoat layer of filter aid is added to the pressure filter media to give a thickness of 2–3 mm. The filtration is done as described above for conventional filtration. The filtration is typically carried out at the same temperature as the above mixing of magnesium silicate, filter aid and diluted crude polyisobutyl phenol, and under pressures of up to 100 psig, preferably in the range of 40–90 psig. The choice of magnesium silicate grade and filter aid type as well as the charge of each can be determined to give a boron concentration in the product below 10 ppm and an acceptable filtration rate for a manufacturing plant. The filtrate containing the diluted polyisobutyl phenol is collected and analyzed for boron.

Water-Filter Aid Method

After adjusting the diluted crude polyisobutyl phenol temperature and concentration in solvent, 0.05–1% diatomaceous earth filer-aid is added to the diluted crude and mixed for about 1–2 hours until the mixture is uniform. The preferred charge of filter aid is 0.1–0.6%, the most preferred charge is 0.2–0.4%, based on the diluted crude polyisobutyl phenol. After the filter aid has been thoroughly mixed into the diluted crude polyisobutyl phenol, water is added to give a concentration of about 100–1500 ppm, preferably about 200–1200 ppm, and most preferably about 250–1000 ppm of water, based on the diluted crude polyisobutyl phenol. Deionized or distilled water is preferred so as not to introduce trace minerals into the product.

Typically, about 0.3 to 12 grams of water will be employed per gram of boron to be removed, preferably about 0.7 to 10 grams, and more preferably about 1.7 to 7 grams of water per gram of boron.

Here, the order of addition is an important consideration. The water should be added after the filter aid is mixed with the diluted crude polyisobutyl phenol. This will ensure that the wetting of the filter aid is uniform and water loss from evaporation is minimal.

The filter aid, water, and diluted crude polyisobutyl phenol are mixed for 0.25–10 hours, preferably for 0.5–3 hours, and most preferably 1–2 hours, at the temperature ranges described above, that is about 20–200° C., preferably about 35–100° C., and more preferably about 40–55° C.

A precoat layer of filter aid is added to the pressure filter media to give a thickness of 2–3 mm. The filtration is done as described above for conventional filtration. The filtration is typically carried out at the same temperature as the above mixing of the filter aid, water and diluted crude polyisobutyl phenol, and under pressures of up to 100 psig, preferably in the range of 40–90 psig. The choice of filter aid type as well as the exact water charge can be determined to give a boron concentration in the product below 10 ppm and an acceptable filtration rate for a manufacturing plant. The filtrate containing the diluted polyisobutyl phenol is collected and analyzed for boron.

A combination of water and magnesium silicate may also be employed with the filter aid in accordance with the process of the present invention. The amount of material charged and the filtration conditions are generally the same as described above. When water is employed in the absence of magnesium silicate, the water should generally be combined with a silica-containing filter aid, such as diatomaceous earth.

Other materials having an activated surface may also be mixed with the filter aid during the filtration step, such as activated carbon (carbon black).

Improvement of Polyisobutyl Phenol Properties

U.S. Pat. No. 4,587,307 describes how low concentrations of impurities in polybutene intermediates can lead to unwanted side reactions in subsequent reaction of the polybutene with maleic anhydride to provide polybutenyl succinic anhydride. It has now been discovered that the Mannich reaction of polyisobutyl phenol with an aldehyde and polyamine is very sensitive to low concentrations of boron in the polyisobutyl phenol. The boron is present in the form of salts that were not completely removed during the purification of the crude polyisobutyl phenol. It has now been found that boron concentrations as low as 29 ppm result in brown insoluble resin deposits on the inside of the reaction vessel. This leads to equipment operability and maintenance problems. For example, fouling of heat exchange surfaces can increase the batch cycle time and potentially result in the eventual failure of the equipment. Deposits on baffles and agitators can degrade the mixing and accelerate deposit formation. The quality of the product is also adversely affected.

In the Mannich reaction, the boron appears to catalyze a condensation reaction of the aldehyde and the polyamine. It has now been surprisingly found that the residual boron concentration must be less than about 10 ppm to ensure that resin deposition in the reactor is not a problem.

U.S. Pat. No. 4,231,759 describes the reaction products obtained from the Mannich condensation of high molecular weight alkyl-substituted hydroxyaromatic compounds, amines and aldehydes for use as detergents in liquid hydrocarbon fuels. In one example in this patent, 1 mole of polyisobutyl phenol derived from convention polyisobutene (900 number average molecular weight) was reacted with 1 mole of diethylenetriamine (DETA) and 3 moles of formaldehyde. The polyisobutyl phenol, DETA, and xylene solvent were mixed and heated to 82–93° C. Aqueous formaldehyde was charged over a period of 30 minutes while maintaining the temperature of the mixture below 93° C. The reaction mixture was then heated to 149–177° C. and held at the final temperature for 2 hours while purging with inert gas to remove all of the water. The reaction product was then cooled, filtered, and diluted with xylene to give a concentration of 40–50% active Mannich product.

To illustrate the problem associated with high residual boron concentrations, an experiment very similar to the example in U.S. Pat. No. 4,231,759 was conducted, except that the polyisobutyl phenol employed was made from polyisobutene (950–1000 number average molecular weight) containing more than 70% methylvinylidene isomer. In addition, the polyisobutyl phenol contained 82 ppm of boron in the form of boron salts remaining from alkylation. At the end of the Mannich reaction, very severe brown resinous deposits were observed on the inside the reactor. There were deposits on the walls, the baffles, the agitator shaft, and the thermocouple. In an attempt to clean the reactor, the deposits were found to be not soluble in any common solvents, such as aromatic solvent, acetone, hexane, toluene, benzene, chloroform, dioxane, tetrahydrofuran, methanol, dimethylformamide, and 100 neutral oil.

In fact, some resins were more difficult to remove than others. The quantity of the resin did not determine the difficulty in removing it. In some cases, there was only a small amount of resin, but it was tightly "glued" to the glass surfaces.

The same propensity to form resin deposits was observed when process conditions (temperature profile) were changed and paraformaldehyde was used in place of aqueous formaldehyde. At a boron concentration of 29 ppm in the polyisobutyl phenol, it was found that resin deposits were becoming noticeable on the internal surfaces of the reactor. When the boron concentration was reduced to below about 10 ppm, there were no resin deposits. The product color was also affected by the amount of boron. As an example, in one case, the color of the starting polyisobutyl phenol was 4 on the ASTM D1500 color scale. The Mannich product had a color of 4.2 and a Mannich compound content of 83% (solvent-free) when the boron content of the polyisobutyl phenol was 5 ppm. Another Mannich sample had a color of 6.4 and a Mannich compound content of 79% (solvent-free) when the boron content of the polyisobutyl phenol was 29 ppm. The effects are more dramatic on the Mannich compound content of the product as the boron content is increased further. At 227 ppm of boron, the Mannich compound content decreased to 53% of the solvent-free product.

All of the previous observations of resin deposition were at a charge mole ratio of 1:1:3 polyisobutyl phenol:DETA:formaldehyde. When the amount of formaldehyde was reduced to give a charge mole ratio of 1:1:2.8 polyisobutyl phenol:DETA:formaldehyde, no resin deposits were observed at boron levels of 31 ppm of boron in the polyisobutyl phenol. However, resin deposits were still severe when the polyisobutyl phenol contained 227 ppm and the amount of formaldehyde was reduced even further to give a molar charge ratio of 1:1:2 for polyisobutyl phenol:DETA:formaldehyde. Thus, high boron concentrations in the polyisobutyl phenol is a significant, but not the only variable that influences resin deposits.

EXAMPLES

The following examples are presented to illustrate specific embodiments of the present invention and synthetic preparations thereof; and therefore these examples should not be interpreted as limitations upon the scope of this invention.

Example 1

Preparation of Crude Polyisobutyl Phenol

Crude polyisobutyl phenol was synthesized in a 30-gal stainless steel batch reactor kettle. The reactor was charged with 45.0 kg (47.34 moles) of Glissopal 1000 polyisobutene. This polyisobutene was manufactured by BASF and contained at least 70% methylvinylidene isomer. The number average molecular weight was about 950–1000. After adjusting the polyisobutene temperature to 45° C., 13.5 kg (143.7 moles) of liquid phenol was charged. The reactor was purged with nitrogen and the temperature of the phenol-polyisobutene mixture adjusted to 43–45° C. The alkylation reaction was performed by charging 303.3 g of $BF_3$-phenol complex to the reactor. The charging of the $BF_3$-phenol complex was staged so as to control the reactor temperature in the range 44–50° C. The total $BF_3$-phenol charge corresponded to 1.183 moles of $BF_3$. After an elapsed time of five hours and 18 minutes from the start of the reaction, 81.2 g of aqueous ammonia (30% $NH_4OH$) was charged to neutralize the $BF_3$ and stop the reaction (about 1.17 mole per mole of $BF_3$). The neutralization was verified by diluting a sample of crude polyisobutyl phenol with hexane, extracting the diluted sample with water, and measuring the pH of the water phase. The measured pH was 7.3. The unconverted phenol and light alkylphenols were removed from the crude polyisobutyl phenol by distillation. The distillation was done by heating the reactor to 160° C. over two hours and nine minutes and at the same time gradually lowering the pressure to 25 millimeters of mercury. The final temperature of 160° C. and final pressure of 25 millimeters of mercury were held for one hour. After breaking vacuum cooling the crude to 85° C., the reactor contents were transferred into one-gallon storage containers for use in the boron removal experiments discussed in the next examples. The boron content of the crude, undiluted polyisobutyl phenol measured by Inductively Coupled Plasma Spectroscopy was 227 ppm. The hydroxyl number by tetrabutylammonium hydroxide titration of a washed sample of the polyisobutyl phenol was 51.8 mg KOH/g (solvent-free basis).

Example 2

Boron Removal from Polyisobutyl Phenol by Water Washing

Following a procedure very similar to Example 1, 45.4 kg (47.79 moles) of Glissopal 1000 polyisobutene and 13.5 kg (143.8 moles) of liquid phenol were charged to the 30-gallon reactor. After adjusting the reactor temperature to 44° C., the alkylation reaction was conducted by charging 302.3 g of $BF_3$-phenol complex to the reactor. As in Example 1, the charging of the $BF_3$-phenol complex was staged so as to control the reactor temperature in the range 44–50° C. The reaction was continued until 93.5 g of aqueous ammonia (30% $NH_4OH$) was charged at five hours from the start of the reaction in order to neutralize the $BF_3$ and stop the reaction. The neutralization was verified by the water extraction method described in Example 1 and gave a pH of 7.5. The unconverted phenol and light alkylphenols were removed by distillation. The distillation step was done by heating the reactor to 160° C. over one hour and 42 minutes while at the same time gradually lowering the pressure to 25 millimeters of mercury. The final temperature and pressure of 161° C. and 25 millimeters of mercury were held for one hour.

After breaking vacuum and cooling the crude polyisobutyl phenol (49.8 kg) to 95° C., 26.8 kg of Exxon Aromatic 100 solvent was charged in order to lower the viscosity of the crude product. Next, the diluted crude product was mixed with 8.4 kg of deionized water (11%, based on the diluted polyisobutyl phenol) for one hour. The agitator was turned off and the water phase was allowed to separate for one hour. After decanting the water phase, another 8.4 kg of deionized water was mixed with the diluted crude product for one hour. After a phase separation time of one hour, the second wash water was decanted from the diluted polyisobutyl phenol. The water phase was decanted. The diluted polyisobutyl phenol was dried by distillation. This was done by gradually increasing the temperature to 105–110° C., and gradually decreasing the pressure to 140 millimeters of mercury over one hour and twenty four minutes. This was enough time to remove all of the water and a small amount of solvent. The product was cooled to 85° C. and removed from the reactor. The finished polyisobutyl phenol contained 73.2% polymer and 26.8% solvent. The polymer contained 6% unconverted polyisobutene and 94% polyisobutyl phenol. Essentially all of the polyisobutyl phenol was monoalkylated phenol with para substitution on the aromatic ring. The boron content of the finished polyisobutyl phenol measured by Inductively Coupled Plasma Spectroscopy was 0.9 ppm. The hydroxyl number by terabutylammonium hydroxide titration was 37.2 mg KOH/g.

Example 3

Conventional Filtration 2588 g of crude polyisobutylphenol from Example 1 was charged to a 5 L jacketed tank. The distilled crude contained 227 ppm of boron. 1114 g of light alkylate solvent was added and was thoroughly mixed with the crude polyisobutylphenol (about 15 minutes) at about 60° C. Light alkylate solvent is an aromatic solvent manufactured by Chevron Chemical S.A. After the solvent and crude polyisobutylphenol were mixed together, 8 g of HyFlo Super Cel diatomaceous earth filter aid was added and thoroughly mixed into the diluted crude. HyFlo Super Cel filter aid is manufactured by Manville Corporation. The diluted crude was mixed with the filter aid for 1–2 hours at 60° C. A pressure filter having an area of $1.113 \times 10^{-2}$ $m^2$ was precoated with 32 g of HyFlo Super Cel filter aid. The crude was charged to the pressure filter and filtered at 50–80° C. and 90 psig. This gave a filtrate rate of 142 $kg/h/m^2$. Analysis of the filtrate showed that it contained 49 ppm of boron.

Example 4

Conventional Filtration

In this test we used a finer grade (smaller particle size distribution) of filter aid than the HyFlo Super Cel from Example 3 for both precoating and admix, and also changed to a lower boiling range solvent. 2600 g of crude polyisobutylphenol from Example 1 were charged to a 5 L jacketed tank. 1115 g of $C_9$ aromatic solvent was added and was thoroughly mixed with the crude polyisobutylphenol (about 15 minutes) at about 60° C. The $C_9$ aromatic solvent was Exxon Aromatic 100 manufactured by Exxon Chemical Company. After the solvent and crude polyisobutylphenol were mixed together, 9.7 g of Celite 512 diatomaceous earth filter aid were added and thoroughly mixed into the diluted crude. Celite 512 filter aid is manufactured by Manville Corporation. The diluted crude was mixed with the filter aid for 1–2 hours at 60° C. A pressure filter having an area of $1.113 \times 10^{-2}$ $m^2$ was precoated with 32 g of Celite 512 filter aid. The crude was charged to the pressure filter and filtered at 60° C. and 90 psig. This gave a filtrate rate of 282 $kg/h/m^2$. Analysis of the filtrate showed that it contained 52 ppm of boron. This is again typical for conventional filtration.

Example 5

Conventional Filtration

In this test we used a finer grade (smaller particle size distribution) of filter aid than HyFlo Super Cel for just the admix and used HyFlo Super Cel for the precoat.

2400 g of crude polyisobutylphenol from Example 1 were charged to a 5 L jacketed tank. 1292 g of $C_9$ aromatic solvent was added and was thoroughly mixed with the crude polyisobutylphenol (about 15 minutes) at about 45° C. After the solvent and crude polyisobutylphenol were mixed together, 9 g of Celite 512 diatomaceous earth filter aid was added and thoroughly mixed into the diluted crude. The diluted crude was mixed with the filter aid for 1–2 hours at 45° C. A pressure filter having an area of $1.113 \times 10^{-2}$ $m^2$ was precoated with 16 g of HyFlo Super Cel filter aid. The crude was charged to the pressure filter and filtered at 40–42° C. and 90 psig. This gave a filtrate rate of 238 kg/h/$m^2$. Analysis of the filtrate showed that it contained 45 ppm of boron. This is again typical for conventional filtration.

Example 6

Magnesium Silicate 2402 g of crude polyisobutylphenol from Example 1 were charged to a 5 L jacketed tank.

1293 g of $C_9$ aromatic solvent was added and was thoroughly mixed with the crude polyisobutylphenol (about 15 minutes) at about 50° C. After the solvent and crude polyisobutylphenol were mixed together, 27 g of Magnesol HMR-LS was charged. Magnesol HMR-LS is a magnesium silicate manufactured by The Dallas Group of America, Inc. Immediately after charging the Magnesol, 4.5 g of HyFlo Super Cel diatomaceous earth filter aid was added and thoroughly mixed into the diluted crude.

The diluted crude was mixed with the Magnesol and filter aid for one hour at 50° C.

A pressure filter having an area of $1.113 \times 10^{-2}$ $m^2$ was precoated with 16 g of HyFlo Super Cel filter aid. The crude was charged to the pressure filter and filtered at 40–44° C. and 90 psig. This gave a filtrate rate of 358 kg/h/$m^2$. Analysis of the filtrate showed that it contained <1 ppm of boron. This is a surprising improvement over conventional filtration. Also, the filtration rate has been improved.

Example 7

Magnesium Silicate

The procedure in Example 6 above was repeated except the quantity of Magnesol and filter aid added with the Magnesol was reduced by 50%. The crude was charged to the pressure filter and filtered at 40–44° C. and 90 psig. This gave a filtrate rate of 347 kg/h/$m^2$.

Analysis of the filtrate showed that it contained <1 ppm of boron.

Example 8

Water and Filter Aid 2400 g of crude polyisobutylphenol from Example 1 were charged to a 5 L jacketed tank. 1292 g of $C_9$ aromatic solvent was added to the tank and was thoroughly mixed with the crude polyisobutylphenol (about 15 minutes) at about 50° C. After the solvent and crude polyisobutylphenol were mixed, 8 g of HyFlo Super Cel filter aid was charged and mixed thoroughly with the diluted crude. 1.87 g of deionized water (506.5 ppm) was charged to the tank and the crude polyisobutylphenol mixture was agitated for one hour at 50° C. A pressure filter having an area of $1.113 \times 10^{-2}$ $m^2$ was precoated with 16 g of HyFlo Super Cel filter aid. The crude was charged to the pressure filter and filtered at 40–43° C. and 90 psig. This gave a filtrate rate of 672 kg/h/$m^2$. Analysis of the filtrate showed that it contained 2 ppm of boron. This is a surprising improvement over conventional filtration in terms of boron content and the filtration rate, and was also a surprise that boron could be reduced without magnesium silicate. However, diatomaceous earth is a natural silicate derived from the skeletons of micro-organisms. The diatomaceous earth is mined and then prepared by high temperature calcination and screening.

Example 9

Effect of Filter Aid Choice on Magnesium Silicate Treatment

The choice of diatomaceous earth filter aid to use with the magnesium silicate can affect the filtration performance due to the relatively small particle size of both the magnesium silicate and boron sediment compared to the particle size of the filter aid. Some typical particle size data were acquired using a Malvern MasterSizer MS20 light-scattering instrument.

|  | Particle Diameter in microns | | | |
| --- | --- | --- | --- | --- |
| Sample | <10% | <50% | <90% | Vol. Mean |
| Clarcel CBL-DIC | 11.6 | 39.4 | 104 | 49.4 |
| HyFlo Super Cel | 9.0 | 33.0 | 90.4 | 42.5 |
| Magnesol HMR-LS | 6.1 | 29.4 | 55.9 | 30.9 |
| Clarcel CBL-CB | 3.6 | 14.0 | 52.9 | 22.6 |
| Example 1 Sediment | 2.8 | 6.3 | 15.2 | 8.3 |
| Plant Sediment 1 | 0.3 | 2.0 | 39.0 | 10.3 |
| Plant Sediment 2 | 1.1 | 2.3 | 39.1 | 10.8 |

Like any filtration, some optimization of the filter aid is needed considering the materials available and the equipment. In this example, we show that substituting a coarser filter aid like Clarcel CBL-DIC filter aid in place of Celite Hy-Flo Super Cel for the precoat layer on the filter screen can affect the filtration and result in boron levels higher than 10 ppm even in the presence of Magnesol.

Diluted crude polyisobutylphenol was produced in a manufacturing plant by the general procedure in Example 1 with the exception that ammonia gas was used for the $BF_3$ neutralization. A $C_9$ aromatic solvent was added to give a nonvolatile residue content of 69.4%. 360 kg of this diluted crude polyisobutylphenol and 24.4 kg of additional $C_9$ aromatic solvent were mixed for 0.5 hour in a 500-L filter feed tank at 50° C. to give a diluted crude of 65% nonvolatile residue content.

0.47 kg of Clarcel DIC filter aid and 2.81 kg of Magnesol HMR-LS were charged to the filter feed tank and mixed with the crude at 50° C. for one hour. A 0.5 $m^2$ Schenk filter was precoated with 0.7 kg of Clarcel DIC filter aid. The crude mixture was filtered at 40–50° C. and a maximum pressure of 54 psig. The average filtration rate was 285 kg/h/$m^2$. The filtered diluted polyisobutylphenol contained 29 ppm of boron.

Example 10

Effect of Filter Aid Choice on Magnesium Silicate Treatment

We repeated the conditions of Example 9 except we precoated the filter with a 0.7 kg-layer of Clarcel CBL-CB on top of a layer of a 0.7 kg-layer of Clarcel CBL-DIC to reduce the large porosity of the filter medium on the filter screen. Clarcel CBL-CB has a much smaller particle size distribution than Clarcel CBL-DIC and does not let the magnesium silicate and boron sediment pass through the filter medium. Although this is an extreme example of changing the filter medium on the filter screen, this shows the importance of matching the proper amount and type of filter aid with the type and amount of magnesium silicate used in the treatment. The crude mixture was filtered at 40–50° C. and a maximum pressure of 54 psig. The average filtration rate was 76 kg/h/m$^2$. The filtrate contained 5 ppm of boron.

Example 11

Effect of Filter Aid Choice on Magnesium Silicate Treatment

We repeated the conditions of Example 9 except we increased the amount of Clarcel CBL-DIC and magnesium silicate by 70% in the treatment mixture itself and made no changes to the filter precoat (the filter medium on the filter screen). Again, this is not an optimized treatment, but does serve to illustrate another example of the importance of using the proper amount and type of filter aid with the selected magnesium silicate. In this case, we compensated for the inadequate precoat medium in Example 10 by increasing the amount of body feed so that a less porous medium is established as the filtration is started. 360 kg of this diluted crude polyisobutylphenol and 24.4 kg of additional C$_9$ aromatic solvent were mixed for 0.5 hour in a 500-L filter feed tank at 50° C. to give a diluted crude of 65% nonvolatile residue content. 0.80 kg of Clarcel DIC filter aid and 4.7 kg of Magnesol HMR-LS were charged to the filter feed tank and mixed with the crude at 50° C. for one hour. A 0.5 m$^2$ Schenk filter was precoated with 0.7 kg of Clarcel CBL-DIC filter aid. The crude mixture was filtered at 40–50° C. and a maximum pressure of 54 psig. The average filtration rate was 80 kg/h/m$^2$. The filtrate contained 5 ppm of boron.

Example 12

Polyisobutylphenol Property Improvement in Mannich Reaction

The processing properties of polyisobutylphenol when reacted with diethylenetriamine and formaldehyde in the mole ratio 1:1:3, respectively, to produce a Mannich base were improved by reducing the concentration of boron below 10 ppm using one of the treatment methods discussed above. In particular, insoluble resin deposition on the inside of the reactor was eliminated and the color of the Mannich base improved (less dark in color) by reducing the boron concentration in the polyisobutylphenol. The polyisobutylphenol samples used to demonstrate this improvement in processing properties are as follows:

| Mannich Experiment Number | PibPhenol Feed Ref. Number | Hydroxyl Number mg KOH/g | Nonvolatile Residue % | Boron Content ppm |
|---|---|---|---|---|
| 8PIB120 | 8PIB115 | 36.6 | 63.7 | 82 |
| MAN-32 | ALK-19-2 | 35.4 | 69.4 | 52 |
| G1893 | G1888 | 36.4 | 65.1 | 29 |

-continued

| Mannich Experiment Number | PibPhenol Feed Ref. Number | Hydroxyl Number mg KOH/g | Nonvolatile Residue % | Boron Content ppm |
|---|---|---|---|---|
| 8PIB129 | 8PIB126 | 38.7 | 64.2 | 7 |
| G1892 | G1890 | 34.1 | 62.4 | 5 |

The Mannich Experiment Number in the above table is the number assigned to the Mannich reaction batch. The PibPhenol Feed Reference Number in the above table is the batch number assigned when the crude polyisobutylphenol was filtered to remove boron sediment. The crude polyisobutylphenols used to make 8PIB115, 8PIB126, G1888, and G1890 were produced in a manufacturing plant by the general procedure in Example 1 with the exception that ammonia gas was used for the BF$_3$ neutralization. The crude used for 8PIB115 and 8PIB126 was from a separate manufacturing lot than the crude used to make G1888 and G1890. ALK-19-2 was made using the crude polyisobutylphenol described in Example1.

The diluted polyisobutylphenol samples 8PIB115 and ALK-19-2 were prepared by conventional filtration following the methods described in Examples 3–5.

The diluted polyisobutylphenol sample 8PIB126 was prepared in the laboratory by the magnesium silicate treatment method as described in Example 6 with the following exceptions. A different filter apparatus was used, but the area was the same. The total diluted crude charge and solvent charge to the filter feed tank at 65% nonvolatile residue was 1703 g. Clarcel CBL-DIC was used in place of Celite HyFlo Super Cel for the diatomaceous earth body feed. The precoat consisted of a base coat of 10 g of CBL-DIC and then 10 g of CBL-CB on top of the CBL-DIC. This replaced the HyFlo Super Cel precoat. The maximum filtration pressure was 80 psig and the average filtration rate was 267 kg/h/m$^2$.

The diluted crude polyisobutylphenol sample G1888 was prepared as described in Example 9 and G1890 was prepared as described in Example 11. G1888 and G1890 are not representative of an optimized magnesium silicate treatment process but give a very useful range of boron content for illustrating the effect on resin formation during the Mannich reaction.

The hydroxyl number analysis of each sample gives the molar concentration of alkylphenol in the polyisobutylphenol. This is needed for calculating Mannich reaction charges because the conversion of polyisobutylene to polyisobutylphenol is less than 100%. The nonvolatile residue analysis can be used to estimate the amount solvent in the diluted polyisobutylphenol. We use these samples to show that as boron concentration is reduced below 10 ppm, resin deposition on the insides of the reactor is eliminated and color darkening of the Mannich product is reduced.

Example 13

Resin Deposition in Mannich Reaction (8PIB120)

700 g of diluted polyisobutylphenol, 8PIB115, containing 82 ppm of boron was charged to a two liter reaction flask equipped with a condenser, Dean-Stark trap, heating mantle, agitator, and temperature control system. The Dean-Stark trap separates and collects water from the condensate and returns any solvent to the reaction mixture. 25.0 g of solvent was added to the Dean-Stark trap at the start so that very little net solvent would be lost to the overheads from the diluted polyisobutylphenol charge. The temperature of the diluted polyisobutylphenol was increased to 60° C. while agitating vigorously. 44.8 g of paraformaldehyde (prill form, 91.93% purity, from Hoechst-Celanese) was quickly added to the diluted polyisobutylphenol and mixed for 15 minutes. The reactor was purged with nitrogen and then a slight vacuum (20 mmHg) applied. 47.3 g of diethylenetriamine (99.5% purity, Lambert Rivière) was added over several minutes from a dropping funnel. After 15 minutes of mixing, the temperature of the reactor was increased to 175° C. over 1.5 hours and then held at 175° C. for 5 hours. Most of the water of reaction distilled overhead during the heat-up and was collected in the Dean-Stark trap. The reactor was cooled to 85° C., and the product was filtered using a ceramic filter funnel and DIC filter aid to remove 0.2 vol % of crude sediment. The inside of the reactor was heavily coated with an insoluble, dark-brown, resinous material.

Example 14

Elimination of Resin Deposition in Mannich Reaction (8PIB129)

The procedure in Example 10 was repeated using 700 g of diluted polyisobutylphenol sample 8PIB126 containing 7 ppm of boron, 47.3 g of paraformaldehyde, and 50.1 g of diethylenetriamine. Again, 25 g of solvent was charged to the Dean-Stark trap. At the end of the reaction there were no dark brown resin deposits on the inside surfaces of the reactor.

Example 15

Resin Deposition in Mannich Reaction (MAN-32)

3085 g of diluted polyisobutylphenol (ALK-19-2), containing 52 ppm of boron, was charged to a 5-L cylindrical glass reactor equipped with baffles, agitator, heating mantle, condenser, Dean-Stark trap, temperature and pressure control system. 41.6 g of Exxon Aromatic 100 solvent was added to the Dean-Stark trap. The diluted polyisobutylphenol was warmed to 60° C. and then 191 g of paraformaldehyde (prill form, 92.5% purity, from Hoechst-Celanese) was quickly charged to the reactor. The diluted polyisobutylphenol and paraformaldehyde were mixed for 15 minutes. 203 g of diethylenetriamine (98.32% purity, Baker Chemical Company) was added to reactor in less than 2 minutes. The reactor head-space was purged with nitrogen and then the pressure control was set to give a slight vacuum. After agitating the reaction mixture for 15 minutes, the temperature was increased to 175° C. over 1.7 hours. The reaction mixture was held at 175° C. for 5 hours and the pressure controlled at 14.3 psia. The crude reaction product was cooled to 50° C. and was found to contain 0.2 vol % sediment. 5 g of Manville HyFlo Super Cel filter aid was mixed into the crude product, and the crude was filtered using the same filter apparatus described in Example 3. The internal parts of the reactor (baffles, agitator, thermocouple, agitator shaft, and the glass surface) were found to be coated with an insoluble dark brown resin that could not be easily removed with typical laboratory solvents.

Example 16

Threshold of Resin Deposition in Mannich Reaction (G1893)

311.7 kg of diluted polyisobutylphenol (G1888) containing 29 ppm of boron was charged to a 500-L stainless steel reaction kettle and 10.2 kg of Total Solvarex 9 aromatic solvent. The reaction kettle is a fully equipped industrial pilot unit with temperature and pressure control systems as well as an overhead condenser system capable of recovering water and returning distillate solvent to the reaction mixture as described in Examples 13–15. In addition to a standard pitched-blade turbine as the agitator, the reactor contained three baffles to facilitate mixing. There was also a helical heat transfer coil inside the reactor for added temperature control of the reaction mixture. It is critical that the surfaces inside this reactor as well as larger scale reactors do not become fouled with deposits. If fouling were to occur, the surfaces are difficult to clean. If the heat transfer surfaces and agitator are not kept clean, batch cycle times increases, mixing becomes poor, and equipment failures due to high temperature fatigue or high loads on the agitator become possible. Therefore there is much incentive in a plant to not form resin deposits in the Mannich reaction.

The diluted polyisobutylphenol was warmed to 60° C. and then 19.8 kg of paraformaldehyde (prill form, 92.1% purity, from Hoechst-Celanese) was charged through the reactor hatch. The reactor was closed and purged with nitrogen. The diluted polyisobutylphenol and paraformaldehyde were mixed for 15 minutes. Using a pump and mass flowmeter, 21.1 kg of diethylenetriamine (99.5% purity, Lambert Rivière) was fed to the reactor smoothly over 13 minutes. After mixing the ingredients for 15 minutes, the temperature of the reaction mixture was increased to 175° C. over 1.5 hours and held at 175° C. and 14.3 psia for 5 hours. Most of the reaction water was recovered in the Dean-Stark trap as the temperature was increased to 175° C. At the end of the 5-hour hold, the pressure was reduced to about 560 mm Hg to reflux solvent and recover remaining traces of water. The crude product containing 0.14 vol % sediment was transferred to a filtration tank and was filtered in a separate system. The filtered product had a color of L6.5 on the ASTM D1500 color scale. Inspection of the inside of the reactor after transfer of the crude product indicated small patches of resin deposited on the top surface of the heat transfer coil, and on the vessel surfaces, agitator shaft, and thermowell just above and below the liquid level area. The deposits were not severe, but were significant enough that the reactor could not be operated under these conditions for a long period without eventually building up heavy deposits on the internal surfaces.

Example 17

Elimination of Resin Deposition in Mannich Reaction (G1892)

302.0 kg of diluted polyisobutylphenol (G1890) containing 5 ppm of boron was charged to the 500-L stainless steel reaction kettle described in Example 16. The same operating procedure described in Example 16 was used in this example. The other charges were 18.8 kg of paraformaldehyde and 20.0 kg of diethylenetriamine. The crude product contained 0.06 vol % sediment. After filtration, the color of the product was L4.5 on the ASTM D1500 color scale. After removing the crude product to the filtration system, the inside of the reactor was inspected through the hatch and found to be very clean. There were no resin deposits visible on any of the internal surfaces of the reactor. In comparing the product in Examples 16 and 17, it was observed that filtered product color was improved and crude sediment has been decreased, both as a result of the reduction in boron from 29 ppm to 5 ppm in the diluted polyisobutylphenol feed.

What is claimed is:

1. A method for removing boron from a boron trifluoride-catalyzed polyalkyl hydroxyaromatic reaction product which comprises:
   (a) diluting the polyalkyl hydroxyaromatic reaction product with an inert solvent to give a polyalkyl hydroxyaromatic reaction product concentration in the range of about 40 to about 80 weight percent;
   (b) filtering the diluted polyalkyl hydroxyaromatic reaction product in the presence of a filter aid in combination with (1) magnesium silicate, (2) water or (3) a mixture of magnesium silicate and water; wherein the water is present during filtration at a concentration of about 100 to 1,500 ppm, based on the diluted polyalkyl hydroxyaromatic reaction product; with the proviso that when water is used in the absence of magnesium silicate, the filter aid is diatomaceous earth; and
   (c) recovering a filtrate containing the diluted polyalkyl hydroxyaromatic reaction product having less than about 10 ppm of boron present.

2. The method according to claim 1, wherein the filter aid is diatomaceous earth.

3. The method according to claim 1, wherein the water is present during filtration at a concentration of about 200 to 1200 ppm.

4. The method according to claim 3, wherein the water is present during filtration at a concentration of about 250 to 1000 ppm.

5. The method according to claim 1, wherein the polyalkyl hydroxyaromatic reaction product is polypropyl or polyisobutyl phenol.

6. The method according to claim 5, wherein the polyalkyl hydroxyaromatic reaction product is polyisobutyl phenol.

7. The method according to claim 6, wherein the polyisobutyl group is derived from polyisobutylene containing at least about 70% of a methylvinylidene isomer.

8. The method according to claim 1, wherein the diluted polyalkyl hydroxyaromatic reaction product is filtered in the presence of a filter aid in combination with magnesium silicate.

9. The method according to claim 8, wherein the filter aid is present at a concentration of about 0.005 to 1 percent and the magnesium silicate is present at a concentration of about 0.05 to 2 percent, based on the diluted polyalkyl hydroxyaromatic reaction product.

10. The method according to claim 1, wherein the diluted polyalkyl hydroxyaromatic reaction product is filtered in the presence of a filter aid in combination with water.

11. The method according to claim 10, wherein the filter aid is present at a concentration of about 0.05 to 1 percent, based on the diluted polyalkyl hydroxyaromatic reaction product.

12. The method according to claim 1, wherein the diluted polyalkyl hydroxyaromatic reaction product is filtered in the presence of a filter aid in combination with a mixture of magnesium silicate and water.

13. The method according to claim 1, wherein the filtering is carried out at a temperature in the range of about 20° C. to about 200° C.

14. The method according to claim 1, wherein the filtering is carried out at a pressure of up to 100 psig.

15. The method according to claim 1, wherein the polyalkyl hydroxyaromatic reaction product is diluted with solvent to give a polyalkyl hydroxyaromatic reaction product concentration in the range of about 50 to about 80 weight percent.

16. The method according to claim 15, wherein the polyalkyl hydroxyaromatic reaction product concentration is in the range of about 60 to about 75 weight percent.

17. The method according to claim 16, wherein the polyalkyl hydroxyaromatic reaction product concentration is in the range of about 65 to about 70 weight percent.

18. The method according to claim 1, wherein the diluted polyalkyl hydroxyaromatic reaction product having less than about 10 ppm of boron present is further reacted with an aldehyde and a polyamine to provide a Mannich condensation product having no resin deposits in the reactor.

* * * * *